US008981018B2

United States Patent
Goldfine et al.

(10) Patent No.: US 8,981,018 B2
(45) Date of Patent: Mar. 17, 2015

(54) INTERNAL MATERIAL CONDITION MONITORING FOR CONTROL

(75) Inventors: Neil J. Goldfine, Newton, MA (US); Vladimir A. Zilberstein, Chestnut Hill, MA (US); Ian C. Shay, Waltham, MA (US); Christopher A. Craven, Bedford, MA (US); David C. Grundy, Reading, MA (US); Volker Weiss, Syracuse, NY (US); Andrew P. Washabaugh, Chula Vista, CA (US)

(73) Assignee: Jentek Sensors, Inc., Waltham, MA (US)

( * ) Notice: Subject to any disclaimer, the term of this patent is extended or adjusted under 35 U.S.C. 154(b) by 1616 days.

(21) Appl. No.: 11/079,912

(22) Filed: Mar. 14, 2005

(65) Prior Publication Data

US 2006/0009865 A1  Jan. 12, 2006

Related U.S. Application Data

(60) Provisional application No. 60/553,473, filed on Mar. 15, 2004, provisional application No. 60/564,316, filed on Apr. 22, 2004.

(51) Int. Cl.
*G01N 27/00* (2006.01)
*G01R 33/00* (2006.01)
(Continued)

(52) U.S. Cl.
CPC ........ *G05D 23/2228* (2013.01); *G05D 23/2439* (2013.01); *G05D 23/26* (2013.01)
USPC ............ 526/59; 324/71.1; 324/200; 324/209; 324/219; 324/222; 324/228; 324/234; 324/239

(58) Field of Classification Search
USPC ............ 436/55, 149–150; 324/200, 209, 219, 324/222, 228, 234–244; 429/12–46
See application file for complete search history.

(56) References Cited

U.S. PATENT DOCUMENTS

| | | | |
|---|---|---|---|
| 4,332,157 A | | 6/1982 | Zemel et al. |
| 4,399,100 A | * | 8/1983 | Zsolnay et al. ................. 422/62 |

(Continued)

OTHER PUBLICATIONS

Goldfine et al., Surface mounted periodic field eddy current sensors for structural health monitoring, 2001, SPIE, Proceedings of SPIE vol. 4335, pp. 20-34.*

(Continued)

*Primary Examiner* — Paul Hyun
*Assistant Examiner* — Robert Eom
(74) *Attorney, Agent, or Firm* — Hamilton, Brook, Smith & Reynolds, P.C.

(57) ABSTRACT

The condition of internal or hidden material layers or interfaces is monitored and used for control of a process that changes a condition of a material system. The material system has multiple component materials, such as layers or embedded constituents, or can be represented with multiple layers to model spatial distributions in the material properties. The material condition changes as a result of a process performed on the material, such as by cold working, or from functional operation. Sensors placed proximate to the test material surface or embedded between material layers are used to monitor a material property using magnetic, electric, or thermal interrogation fields. The sensor responses are converted into states of the material condition, such as temperature or residual stress, typically with a precomputed database of sensor responses. The sensor responses can also be used to determine properties of the test material, such as electrical conductivity or magnetic permeability, prior to conversion to the material state. The states are used to support control decisions that control the process or operation causing the material condition to change.

22 Claims, 9 Drawing Sheets

(51) Int. Cl.
  *G01B 7/00*    (2006.01)
  *G05D 23/22*   (2006.01)
  *G05D 23/24*   (2006.01)
  *G05D 23/26*   (2006.01)

(56) References Cited

U.S. PATENT DOCUMENTS

| | | | |
|---|---|---|---|
| 4,453,405 A | 6/1984 | Zemel | |
| 4,551,425 A | 11/1985 | Zemel | |
| 4,814,690 A | 3/1989 | Melcher et al. | |
| 4,891,591 A * | 1/1990 | Johnston et al. | 324/234 |
| 5,453,689 A | 9/1995 | Goldfine et al. | |
| 5,528,155 A * | 6/1996 | King et al. | 324/713 |
| 5,793,206 A | 8/1998 | Goldfine et al. | |
| RE36,986 E | 12/2000 | Melcher | |
| 6,188,218 B1 | 2/2001 | Goldfine et al. | |
| 6,380,747 B1 | 4/2002 | Goldfine et al. | |
| 6,486,673 B1 | 11/2002 | Goldfine et al. | |
| 6,657,429 B1 | 12/2003 | Goldfine et al. | |
| 6,784,662 B2 | 8/2004 | Schlicker et al. | |
| 6,952,095 B1 | 10/2005 | Goldfine et al. | |
| 2002/0075006 A1 | 6/2002 | Goldfine et al. | |
| 2002/0158626 A1 | 10/2002 | Shay et al. | |
| 2002/0163333 A1 | 11/2002 | Schlicker et al. | |
| 2003/0080744 A1 | 5/2003 | Goldfine et al. | |
| 2003/0129763 A1 * | 7/2003 | Chamberlain et al. | 436/149 |
| 2004/0225474 A1 | 11/2004 | Goldfine et al. | |
| 2005/0083032 A1 | 4/2005 | Goldfine et al. | |
| 2005/0171703 A1 | 8/2005 | Goldfine et al. | |

OTHER PUBLICATIONS

Kim et al., Dielectric cure monitoring for glass/polyester prepreg composites, Composite Structures, vol. 57, Issues 1-4, Jul. 2002, pp. 91-99.*

Mohsen, Safari-Ardi, Dielectric characterization of composites based on coated conducting fibres embedded in epoxy matrix, Iranian Polymer Journal, vol. 5 No. 3 (1996), pp. 165-173.*

* cited by examiner

INTERNAL MATERIAL CONDITION MONITORING FOR CONTROL

RELATED APPLICATIONS

This application claims the benefit of U.S. Provisional Application Nos. 60/553,473 filed Mar. 15, 2004 and 60/564,316 filed Apr. 22, 2004, the entire teachings of which are incorporated herein by reference.

BACKGROUND OF THE INVENTION

The technical field of this invention is that of nondestructive materials characterization as applied to control of a process that changes the material properties. The nondestructive characterization provides a quantitative, model-based assessment of surface, near-surface, and bulk material condition for flat and curved parts or components. Characterization of bulk material condition includes (1) measurement of changes in material state, such as degradation/damage caused by fatigue damage, creep damage, thermal exposure, or plastic deformation; (2) assessment of residual stresses and applied loads; and (3) assessment of processing-related conditions, for example from component assembly or heat treatment. It also includes measurements characterizing material states, such as temperature. Characterization of surface and near-surface conditions includes measurements of surface roughness. Each of these includes detection of electromagnetic property changes associated with either microstructural and/or compositional changes, or electronic structure (e.g., Fermi surface) or magnetic structure (e.g., domain orientation) changes.

Manufacturing processes, such as a heat treatment or cold working, are commonly performed on materials in order to introduce beneficial characteristics, such as a desired hardness level or a residual stress distribution. Often, the beneficial characteristics, such as the residual stress from a cold work procedure, are hidden beneath the surface and spatially varying with depth into the material. Furthermore, these processes are often performed in a batch mode according to a preset processing schedule, with only an occasional post-process inspection or destructive evaluation performed to ensure material quality.

Similarly, many material systems and devices have multiple material layer or embedded materials and applying a process or operation of these systems can lead to material changes hidden from the surface. One example is for electronic materials, where temperature excursions due to power dissipation can lead to changes in the conductivity of the conducting pathways and inadvertent signal voltage decay (commonly called IR drop). This thermal or signal degradation is often predicted from simulation models so that it can be avoided during the build-up of the final product. It is typically not possible to embed thermal sensors themselves due to limited space or accessibility, and the state of the devices using these materials is usually obtained from the variations in the electrical signals.

Another example system is a solid oxide fuel cell (SOFC). SOFCs act as energy devices and usually contain stacks of individual cells connected together, with each cell containing a multiple layer system containing anode, electrolyte, cathode, and interconnect materials. The anode, cathode, and interconnect are electronic conductors while the electrolyte is an oxygen-ion conductor. SOFCs typically operate at relatively high temperatures near 1000° C. Advanced systems are highly instrumented and designed to obtain system level operational information such as stack and row voltages and currents, temperature, air and fuel gas composition and flow rates, system pressure and many other parameters. The overall health of such systems during operation is monitored mainly by combining information regarding stack and row voltages, currents and stack temperatures from various locations within the stack. While this methodology is very successful at obtaining a real-time health report of the SOFC power system, it provides little information on the health of individual cells.

Standard characterization techniques for layered electronic materials typically involve microstructural characterization and, in some cases, electrochemical characterization. Microstructural characterization, usually performed as part of a quality control process, typically involves resin-mounting sections of the materials using appropriate metallographic techniques followed by polishing and scanning electron microscopy. For example, electrode porosity is usually measured using the line intercept technique, by drawing several lines on the micrograph of the polished sections at equal angular intervals and measuring the fraction of the line inside pore space to the total length of the line. Other techniques of measuring pore volume fraction from polished cross sections of electrodes include using quantitative metallography techniques with macros that can be set up in software packages. These microstructural characterization techniques can provide comprehensive information about many features of the materials, including layer thicknesses, layer porosity, and adherence of layers. However, these techniques are destructive and slow, typically taking from seven to ten days to complete.

A common way to nondestructively characterize conducting materials is to use eddy-current methods. Conventional eddy-current sensing involves the excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

Existing magnetic/electromagnetic, diffraction, ultrasonic and other methods for assessment of residual stresses or monitoring of applied stress over wide areas are not yet practical or cost-effective. Typically, discrete strain gages are mounted directly onto the material under test (MUT). However this requires intimate fixed contact between the strain gage and the MUT and individual connections to each of the strain gages, both of which limit the potential usefulness for monitoring stress over large areas. Furthermore, strain gages are limited in durability and do not always provide sufficient warning of gage failure or malfunction. Correlations between magnetic properties and stresses in ferromagnetic materials have been studied for over 100 years. Magnetostriction effect data suggests that, depending on the magnitude and sign of the magnetostriction coefficient, correlation between stress and magnetic permeability within certain ranges of the magnetic field should be present. However, attempts to use conventional inductive, i.e., eddy-current, sensors for assessment of residual stresses as well as for a number of other applications have shown significant limitations, particularly for complex geometry components.

SUMMARY OF THE INVENTION

Aspects of the methods described herein involve nondestructive condition monitoring of materials. These conditions or states are for material buried or hidden from the surface and include temperature, stress, damage, damage precursor states and usage states. The material condition is typically assessed through databases generated from models for the sensor response or correlations with independent estimates of material properties, such as electrical conductivity, dielectric permittivity, magnetic permeability, and thermal conductivity. These states are then used to support control decisions for the process being performed on the material that alter the states.

In an embodiment, a test material has at least two layers and a sensor, placed proximate to one material layer, to monitor a state of the farther or hidden material layer. The state that is selected to be monitored changes in response to a process performed on the test material. The sensor response is used to assess or determine the state using a database of precomputed responses generated from a model for the sensor and the test material. The sensor response is also used to support control decisions. In an embodiment, the control action involves setting a goal for the state and adjusting the process to move the state toward the goal. In embodiments, this goal is time varying or spatially varying. In a particular embodiment, the state is temperature and the goal is a temperature value. In an embodiment, the process is a manufacturing process, such as heat treatment or shot peening. The surface and hidden layers can then be layered representations of the process affected areas, such as the residual stress distribution with depth into the material. In another embodiment the process uses the material to perform a functional operation, such as generating electricity as a fuel cell. In embodiments, the sensor is permanently mounted to the test material or embedded between material layers. In another embodiment, one material layer is used to assess the condition of a interface between two materials. For the interface, the selected state can be the integrity of the bond between the layers.

In another embodiment, the test material has at least two component materials with one of the materials embedded in a matrix of a second material. A state is monitored with a sensor during a process that changes this state and used to support control decisions. In an embodiment, the state is the temperature at the interface between the embedded material and the matrix. In another, the embedded material is a fiber and the state is the integrity of the bond between the fiber and the matrix. In another embodiment, a coating is added to the embedded material, prior to embedding, to enhance the observability of the bond between the embedded material and matrix material with a sensor. In yet another embodiment, the state is a cure state, usually of the matrix material. The sensor can use magnetic, electric, or thermal fields to interrogate the material.

In one embodiment, the temperature of a test material having at least two distinct materials is controlled. This involves placing a sensor near the test material and generating a precomputed database of responses using a model for the sensor response that relates an absolute material property, such as an electrical conductivity, to the temperature for each distinct material. A process is then performed that changes the temperature of the test material, with the absolute property for each distinct material having different thermal coefficients or temperature dependencies. By monitoring the sensor response, the temperature is controlled by taking the appropriate control actions. In an embodiment, the test material is an operating device. In another, the test material has multiple material layers. In yet another, the test material has a first material embedded in a matrix of a second material.

In yet another embodiment, a sensor is placed near a test material and the test material has an interface hidden from the surface where the sensor is positioned. The sensor measures an absolute property of the material near the interface by projecting an interrogating field into the test material that penetrates to the hidden interface. The absolute property is dependent upon the usage state at the interface and affects the signal received by the sensor. In embodiments, the usage state is temperature, stress, and cure state. In other embodiments, the interrogating field is magnetic, electric, or thermal. In yet another embodiment, the material is nominally uniform but is modeled or abstractly represented by layered materials. An absolute property of each material layer is then measured, assuming that the thickness of each layer is assumed. Furthermore, in another embodiment, a model is used to generate a database that relates the sensor responses to an absolute property of each material layer.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

This invention is directed toward the nondestructive characterization of a material system for the purpose of controlling the functional operation or performing a process on a material. The material system can have multiple component materials, such as a multiple layer geometry, or it can have one material, such as a fiber or a fiber weave, embedded within a matrix of another material. Generally, the test material either has component materials that have different absolute electric, magnetic or thermal properties or can be modeled or represented with material regions or layers having different absolute properties. A sensor placed near the material system can then preferentially monitor the property changes in one of the materials or model layers while a process is performed on the material system. In this context, the process changes a kinematic, environmental, or physical state of the test material. This is done by processing the material system, for example with a heat treatment or shot peening process, or with a functional operation of the material, such as the typical operation of a fuel cell at elevated temperatures. The properties monitored by the sensor are then related to a state of the system, such as the temperature or residual stress level, and used to control the process, such as altering the applied temperature, the peening duration, or the output current.

Figure 1:
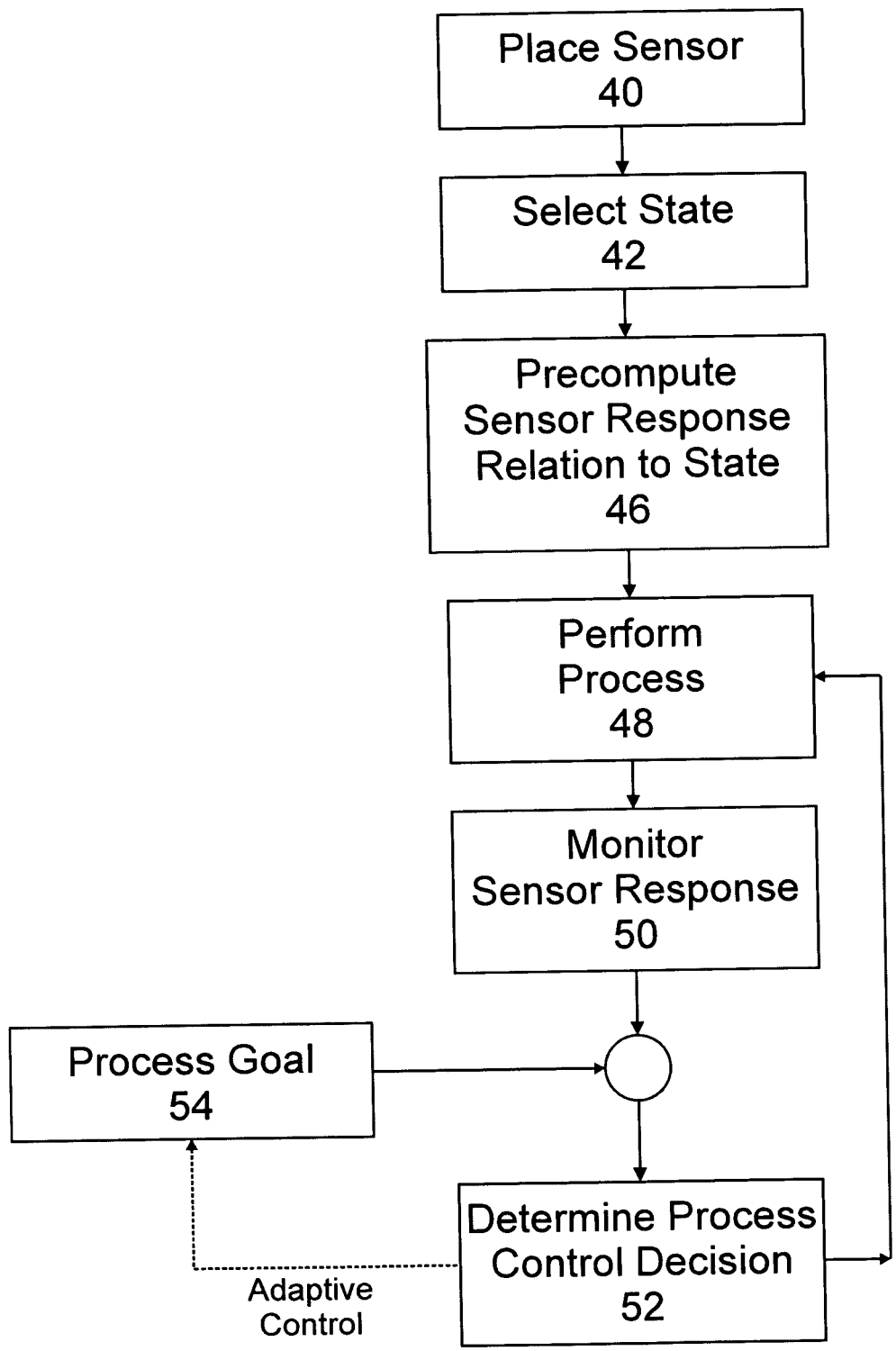
FIG. 1 shows a schematic outline for combining a precomputed database of sensor responses with process control.

An example procedure that uses this approach is illustrated in FIG. 1. The first step in the procedure involves placing a sensor near a material system 40. The material may have distinct or discrete phases, such as layers of differing materials or embedded components, or it may have a gradual change in properties, such as a residual stress distribution with depth, that can be represented by a multiple layer geometry. Next, a state that is to be monitored is selected 42, typically for a hidden or embedded material, that is not directly accessible from the outside surface. Typical states are usage, damage, or damage precursor states, such as temperature or stress. A model based method is used to then precompute a database that relates the sensor response to the state 46. This relation may involve an intermediate calculation where the sensor response is first converted into material or geometric properties, such as an electrical conductivity, magnetic permeability, thermal conductivity, dielectric permittivity, or layer thickness, which is then correlated with the state of interest. A process is then performed on the material system 48, with the sensor responses monitored 50 and used to determine or support any process control decisions 52. These control decisions are obtained from a combination of a process goal 54 along with the states obtained from the sensor responses and can be used in a feedback configuration to alter the process as necessary. Part of the control decision may be adapting or adjusting the process goal or objective. If a model is being used for the process, the model itself may be changed or adapted to the observed behavior based on the sensor information as a model referenced adaptive control. Note that the precomputation of the database of responses permits a rapid inversion of sensor responses into system states suitable for process control.

One example process suitable for the control with this method is shot peening. Shot peening is a commonly used process for introducing compressive residual stresses at the surface of fatigue-critical areas of components. In this process, a high-velocity stream of small beads (shot) or a special flapper tool is used to plastically deform a near-surface layer. The intensity of the shotpeening process depends upon the velocity of the beads, the impingement angle against the material surface, and the duration time. It is generally measured with Almen strips placed at various positions around the part. Within the plastically deformed, i.e. cold worked layer, high compressive residual stresses are introduced; these compressive stresses are balanced by tensile residual stresses in the unaffected "substrate", that is in the base metal which has not undergone cold work during shotpeening. Thus, the residual stress varies with depth into the material and the corresponding stress-dependent absolute material properties, such as electrical conductivity or magnetic permeability, also vary with depth into the material. However, the shotpeening also damages the surface and increases the surface roughness. A typically manufacturing process needs to provide a balance between sufficient peening to introduce the desired residual stresses into the material while limiting excessive peening of areas that can introduce undesired surface roughness and damage. This process can be controlled by measuring the residual stress of a layer or a portion of the material hidden beneath the surface, either with a sensor mounted on the opposite side of the surface being peened or by periodically halting the peening and moving a sensor into position. If the stress level is too low, then the control action could be to increase the velocity or the duration for the process and monitoring the stress until the appropriate stress level is reached. This helps prevent excessive peening. Similarly, if the impingement angle is too low the beads may burrow into the surface so that the stress level is too low for the corresponding surface roughness. Then, the control action would be to increase the impingement angle for the shot.

As another example, consider typical solid oxide fuel cell having numerous individual cells stacked together to increase efficiency. During the manufacturing process, mechanical stresses or damage can be introduced during assembly which can shorten the operating life for both the individual cells and the device. With sensors mounted onto some of the individual cell surfaces, stresses on critical internal materials can be monitored to ensure that they are within acceptable bounds. If the stress state is too high, an example control action could be to disassemble and then reassemble the stack or to place additional or thicker attachments between the individual cells. During functional operation, an air and fuel gas passes through each individual cell to generate electrical energy which also elevates the temperature. Sensors can be used to monitor the temperature of internal interfaces for each individual cell to ensure that the temperatures remain at acceptable levels. If one or more of the individual cells becomes damaged and begins to operate at an excessive temperature, then the control action can be to operate the device at a reduced output until a repair opportunity becomes available. Alternatively, another control action could be to isolate the damaged cell, possibly by reducing the gas flow to that particular cell, so that nearby cells are not also damaged.

The process goal or set point can take a variety of forms. One of the aims of the process control being to effect significant life-cycle cost savings, with the control actions aimed at extending the life for material components. The control goal may be to ensure that conditions that would cause accelerated damage are avoided, such as an over-temperature situation at a buried interface. Furthermore, costly maintenance or replacement actions based on time in service rather than material condition may be avoided. In this form, one of the control decisions may be an action to move the state towards a specified value, such as an operating temperature at an interface or which is spatially varying. This goal does not need to be constant with time and may be time varying. It may even be a trajectory of states that need to be followed, such as a thermal history as part of a heat treatment process. It can include, for example, monitoring the temperature at a buried interface between a coating and a substrate during a coating process. This may also involve controlling the heating and cooling cycle during a metal spraying process, with the sensor behind a substrate, to ensure that the interface temperature and residual stresses at the coating interface follow a predetermined goal. The goal may be a nonlinear transient trajectory of the temperature with time.

Figure 2:
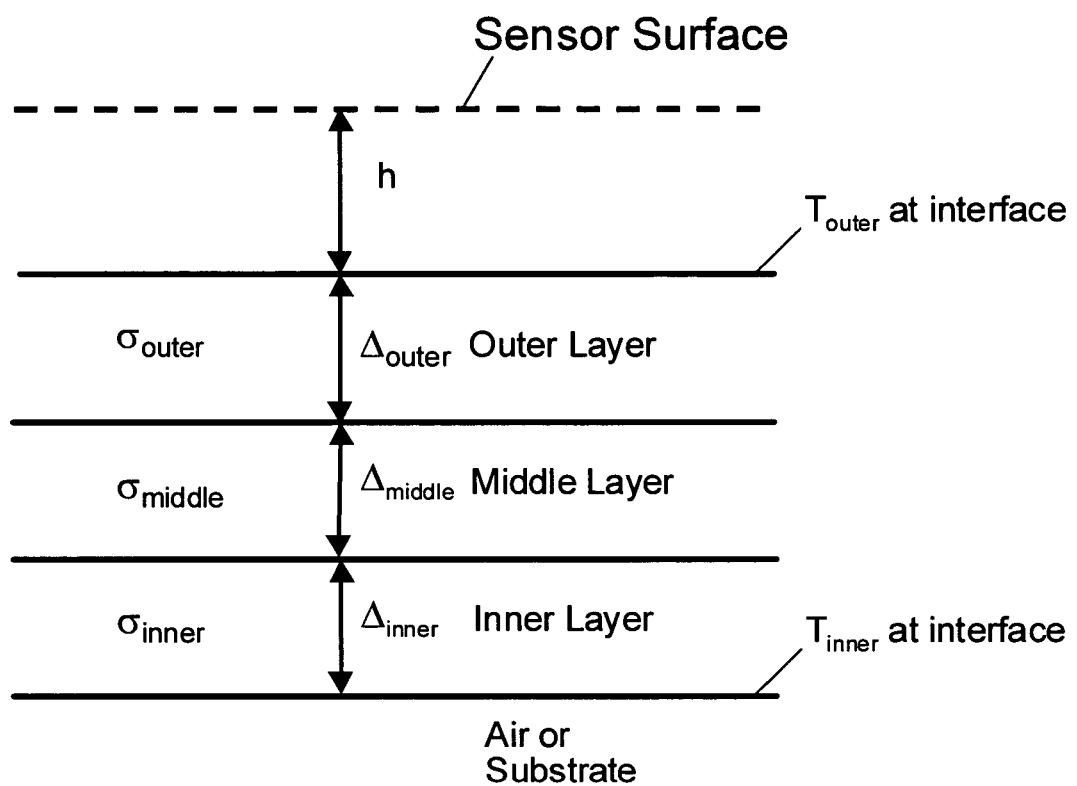
FIG. 2 shows a multiple layer representation for a test material.

FIG. 2 shows a multiple material layer representation of a nominally homogeneous test material. In this case the distribution of a usage state, such as temperature, stress, or cure state varies within the test material. A sensor is placed near an outer surface interface of the test material and the test material is subdivided into outer, middle, and inner layers. This abstract layered representation for the usage state variation with depth allows the usage state at different depths from the outer surface to be determined. These layers may span the entire thickness of the test material so that the lowermost region is air, or these layers may be over a material substrate. Each of these layers has a defined thickness ($\Delta$) and at least one absolute material property that can be measured, such as an electrical conductivity, magnetic permeability, dielectric permittivity, or thermal conductivity. In FIG. 2, the thickness of each layer is predetermined and assumed known so that the electrical conductivity ($\sigma$) of each layer is determined. Using a relation that describes how this absolute property varies with usage state, such as temperature, then allows the usage state at the inner material interface to be determined. Furthermore, the thickness of the inner layer can be made very small compared to the thicknesses of the other material layers, such as the outer and middle layer, so that the absolute property of the inner material layer provides a better measure of the usage state for the inner interface. This use of a thin material layer improves the sensitivity to the state of the interface since bulk absolute property measurements for thick layers may not accurately reflect the interfacial condition. Note that the sensor does not need to be in contact with the outer surface of the test material and the sensor proximity of lift-off (h) may be a property to be determined.

This type of layered media representation is well suited to the monitoring of bond integrity between materials. This is particularly true when the thickness of the inner zone is made thin compared to the thickness of the other layers so that the properties estimated for the inner layer accurately reflect the interfacial conditions. The residual stress in this interfacial layer will change depending upon the bond integrity, as the load transfer into the substrate will change if the bond is locally poor.

As one embodiment, this invention addresses the need for enhanced monitoring and thermal management of electronic materials. For multiple layer electronic materials the sensor may be embedded between layers or placed on surfaces and used to control thermal management actions, such as cooling or changing the operational state. For example, if an area of a circuit board is overheating, then an embedded sensor network could be used to redirect processing so that the heating is more uniform or that the circuit takes better advantage of thermal management resources.

In the area of SOFC health monitoring, model-based sensors can provide early detection of locally degraded regions, both from manufacturing processes as well as from functional operational processes. During manufacture, sensors mounted to or scanned over a material surface may be used for quality control by monitoring the residual stresses, particularly during stack assembly or lay up. During operation, health monitoring can be accomplished either during shutdowns, using scanning sensors, or on-line, using permanently mounted high-temperature sensors. In both cases, the sensors can monitor material degradation. In the case of the high-temperature sensors, however, SOFC operating parameters and/ or process dynamics can be monitored. Both modes of SOFC health monitoring allow for timely detection of failing fuel cell elements and identification of the root cause(s) of failures. The key is to monitor all relevant usage, damage and precursor states, as described for example in U.S. patent application Ser. No. 10/763,573, filed on Jan. 22, 2004, the entire teachings of which are incorporated herein by reference. For fuel cells, usage states include temperature and stress, while damage states may include microstructural changes, cracking, and local corrosion, and precursor states may include initial microstructural variations and residual stresses.

The combination of the high operating temperature and current density can affect electrode microstructure in a SOFC. This can shift the current density distribution in the cells which in turn can alter the temperature distribution in the stack. Destructive analysis of cells after long-term operation often reveals significant microstructural distribution changes particularly at the interfaces between the electrodes and electrolyte of the cell. In particular, long-term operation results in densification of the cathode and reduction in porosity at the cathode-electrolyte interface. This type of microstructure variation for individual cells in the stack is typically not monitored. For example, the stress distribution between the various cell component layers as a function of time or position in the stack, or during involuntary or voluntary thermal cycling of the stack. Similarly, the temperature at buried interfaces within the cell during operation is not monitored primarily because of limited accessibility. Being able to monitor changes in stress distributions and temperature at individual cells in the stack (and near interfaces within those cells) in real time can provide an indication of the health of the device. Such a sensor can provide information which can be used not only to take corrective action during operation, such as reducing the current drawn from individual cells, but also in the design of SOFC cell and stack components, possibly by indicating when individual cells need to be replaced.

A variety of sensors can be used to create the field for interrogating the material and assessing the material condition, such as electric, magnetic, or thermal fields. The type of field to be used depends upon on the properties of the test material, the environment, and the condition of interest. In some cases, multiple sensing fields can be used to assess complementary properties of the test material, as described for example in U.S. patent application Ser. No. 11/036,780, filed on Jan. 14, 2005, the entire teachings of which are incorporated herein by reference.

Figure 3:
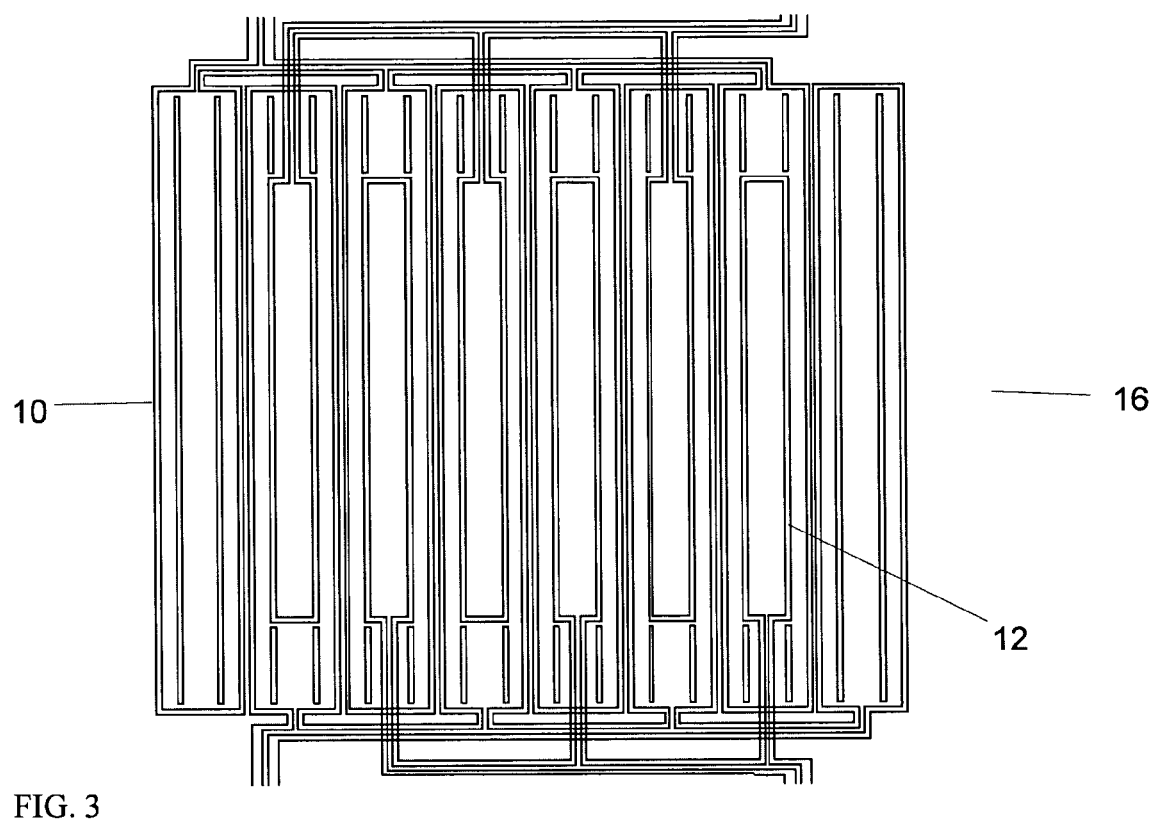
FIG. 3 shows a drawing of a spatially periodic field eddy-current sensor.

An example magnetic field sensor that operates in the magnetoquasistatic (MQS) regime is shown in FIG. 3. This meandering winding magnetometer (MWM®) is a "planar," conformable eddy-current sensor that was designed to support quantitative and autonomous data interpretation methods. The sensor 16 is described in U.S. Pat. Nos. 5,453,689, 5,793,206, and 6,188,218 and U.S. patent application Ser. Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength $\lambda$. A current is applied to the primary winding to create a magnetic field and the response of the MUT to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength λ. For an MWM-Array, the responses from individual or combinations of the secondary windings can be used to provide a plurality of sense signals for a single primary winding construct as described in U.S. Pat. No. 5,793,206 and Re. 36,986, incorporated herein by reference.

Figure 4:
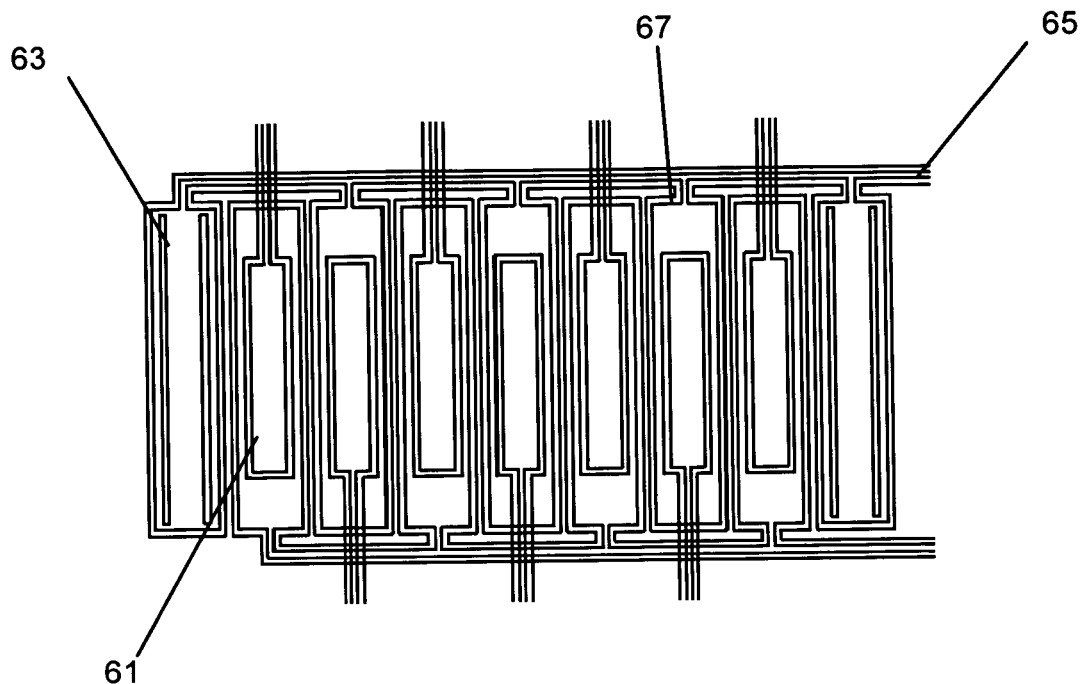
FIG. 4 shows a plan view of sensor array with a single primary winding and an array of sensing elements with connections to each individual element.

The MWM-Arrays typically have one or more drive windings, possibly a single rectangle, and multiple sensing elements for inspecting the test material. Some of the motivation for the use of multiple sensing elements is to increase the spatial resolution of the material being characterized without loss of coverage, to add additional information for use in the estimation of multiple unknown material properties, and to cover large inspection areas in a faster time. Example scanning sensor arrays are described in detail in U.S. patent application Ser. No. 10/102,620, filed Mar. 19, 2002, and Ser. No. 10/010,062, filed Mar. 13, 2001, the entire teachings of which are incorporated herein by reference. FIG. 4 shows a schematic view of a permanently mounted seven-element array. Connections are made to each of the individual secondary elements 61. Dummy elements 63 are placed on the outside meanders of the primary 65. As described in U.S. Pat. No. 6,188,218, the secondaries are set back from the primary winding connectors 67 and the gap between the leads to the secondary elements are minimized.

An efficient method for converting the response of the MWM sensor into material or geometric properties is to use grid measurement methods. These methods map two known values, such as the magnitude and phase or real and imaginary parts of the sensor impedance, into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes. The properties to be determined could also be states, such as usage, damage, or damage precursor states.

An advantage of the measurement grid method is that it allows for near real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 5:
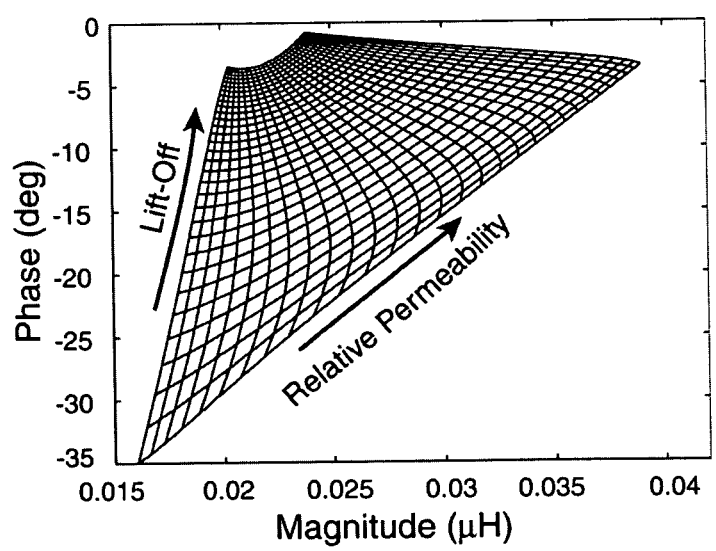
FIG. 5 shows a representative measurement grid relating the magnitude and phase of the sensor terminal impedance to the lift-off and magnetic permeability.
Figure 6:
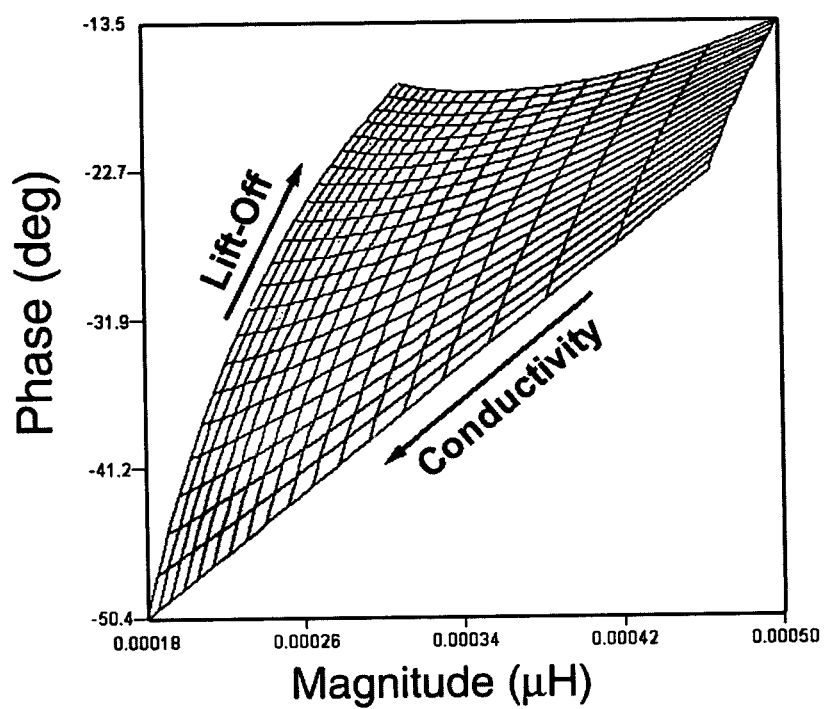
FIG. 6 shows a representative measurement grid relating the magnitude and phase of the sensor terminal impedance to the lift-off and electrical conductivity.

For ferromagnetic materials, such as nickel, cobalt and most steels, a measurement grid can provide a conversion of raw data to magnetic permeability and lift-off. A representative measurement grid for ferromagnetic materials is illustrated in FIG. 5. A representative measurement grid for a low-conductivity nonmagnetic alloy (e.g., titanium alloys, some superalloys, and austenitic stainless steels) is illustrated in FIG. 6. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability). The variation in the coating can be corrected at each point in the image to improve the measurement of permeability in the substrate for the purpose of imaging stresses. The effective property can also be a layer thickness, which is particularly suitable for coated systems. The effective property could also be some other estimated damage state, such as the dimension of a flaw or some indication of thermal damage for the material condition.

Figure 7:
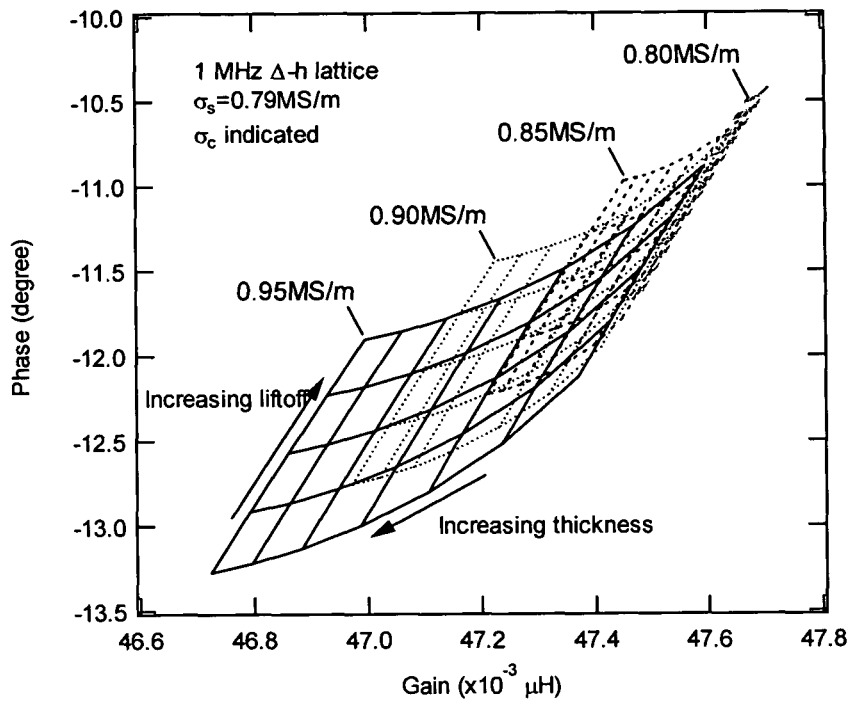
FIG. 7 shows a representative coating thickness/lift-off grid lattice for turbine blade materials.

As an example of a grid lattice, used for characterizing conducting coatings, measurement grids are created for a range of coating conductivities that span the range of interest for a given material, forming a three-dimensional database for the sensor response. A representative grid lattice for the characterization of turbine blade coatings is shown in FIG. 7. The lattice shows coating thickness-lift-off grids for four coating conductivities at a single frequency. In each measurement grid, the spacing between the grid points illustrates the sensitivity for independently estimating the coating thickness and the lift-off. The grid spacing and sensitivity is large when the coating and the substrate have significantly different conductivities; the grid collapses when the conductivities of the coating and the substrate are equal, which is expected for an uncoated specimen. Typically a grid lattice is created for each excitation condition that provides sensitivity to different depths of the penetration for the interrogating field. This can be accomplished with different excitation frequencies or multiple sense elements that are sensitive to different components or segment of the interrogating field. These different excitations are then combined in order to provide a single estimate of the properties that is consistent with each excitation condition.

Figure 8:
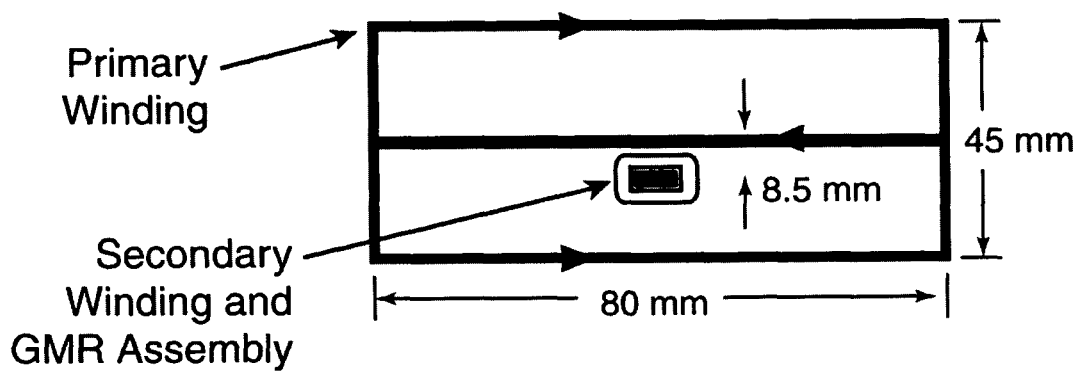
FIG. 8 shows a layout for a single turn Cartesian geometry GMR magnetomer.

In addition to inductive coils, other types of sensing elements, such as Hall effect sensors, magnetoresistive sensors, SQUIDS, and giant magnetoresistive (GMR) devices, can also be used for the measurements. The use of GMR sensors for characterization of materials is described in more detail in U.S. patent application Ser. No. 10/045,650, filed Nov. 8, 2001, the entire teachings of which are incorporated herein by reference. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations. An example rectangular or Cartesian-geometry GMR-based magnetometer is illustrated in FIG. 8.

Figure 9:
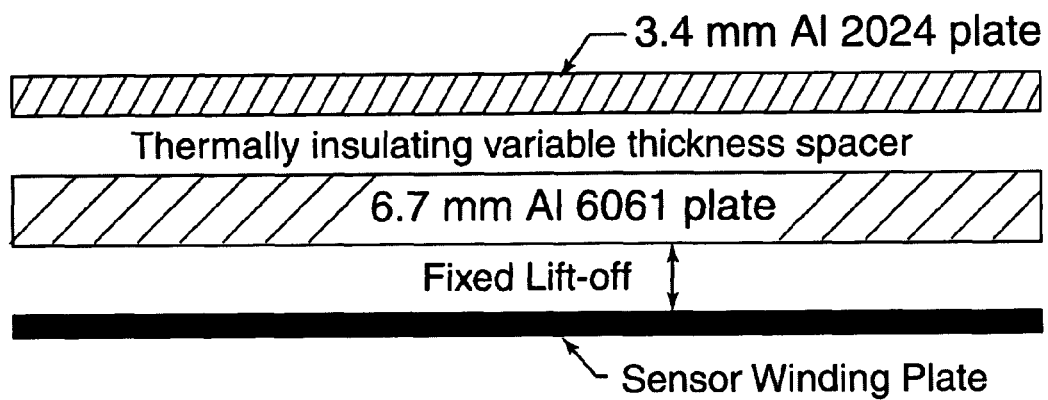
FIG. 9 shows a schematic for remotely monitoring the temperature of a plate.

One example application using a GMR sensor is for monitoring properties through intermediate layers of metal. In this case, the absolute electrical properties are measured through thick metal plates and then related to other physical properties of interest. FIG. 9 shows one such layered geometry, with a low frequency (100 Hz) measurement used to remotely monitor the temperature dependent conductivity variation of an aluminum plate through a 6.3 mm (0.25 in.) thick aluminum plate. The magnetic field from the sensor is projected through the near plate to interrogate and sense the properties of the farther plate. The thickness of the upper plate (remote from the sensor), the conductivity and thickness of the bottom plate (near the sensor), as well as its lift-off (proximity) from the sensor windings, are incorporated in the model used to generate the appropriate measurement grids. The two unknown properties monitored during testing were the conductivity of the upper plate and the thickness of the thermally insulating nonconducting spacer between the two plates, which also varied significantly with the temperature of the upper plate. The ability to measure the two unknown parameters independently was demonstrated by taking measurements at room temperature with spacers of varying thickness and observing that the data follow a constant-conductivity line in the grid. Similar measurements were performed to monitor stress variations on a hidden steel layer in a thick structure, where the stress dependent magnetic permeability of the hidden layer was monitored. Thus, the remote monitoring of the temperature or stress of the hidden layer then allows control action to maintain or alter the temperature or stress on the hidden layer.

Figure 10:
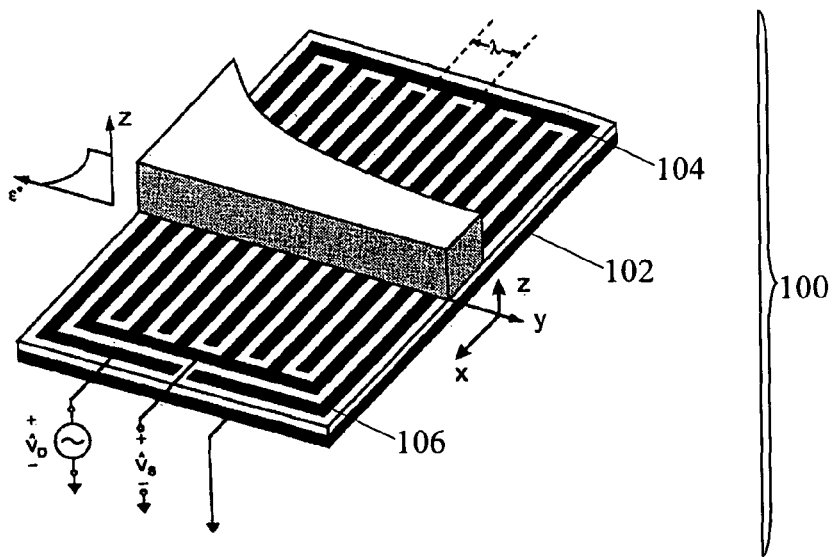
FIG. 10 shows a representative single wavelength interdigitated electrode dielectrometer with spatially periodic driven and sensing electrodes of wavelength $\lambda$ that can measure dielectric properties of the adjacent material.

For insulating or weakly conducting materials such as many ceramics or fiberglass composites, capacitive or dielectric sensors can be used. The sensors are the electromagnetic dual to the inductive sensors, with electric fields taking the place of magnetic fields for inspecting the materials and can be used to monitor stress or temperature, moisture content or contamination or overload of fatigue in adhesives, epoxies, glass, oil, plastics and in single or multiple layered media. In particular, the dielectric properties of many materials changes with cure state, so that single sided dielectrometry measurements can be used for monitoring and control of the curing materials. Here the conductivity and dielectric constant or complex permittivity and layer thicknesses are measured using the same methods as for magnetic field sensing, except that the sensors operate in the electroquasistaic (EQS) regime. A representative single sided sensor geometry is shown in FIG. 10. The application of a sinusoidally time varying potential of angular frequency $\omega = 2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, and 6,486,673 and in U.S. patent application Ser. No. 10/040,797, filed Jan. 7, 2002, and Ser. No. 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $v_D$ while the other, 106, is connected to a high-impedance buffer used to measure the magnitude and phase of the floating potential $v_S$ or to a virtually grounded amplifier to measure the magnitude and phase of the terminal current I. The periodicity of the electrode structure is denoted by the spatial wavelength $\lambda = 2\pi/k$, where k is the wavenumber.

Figure 11:
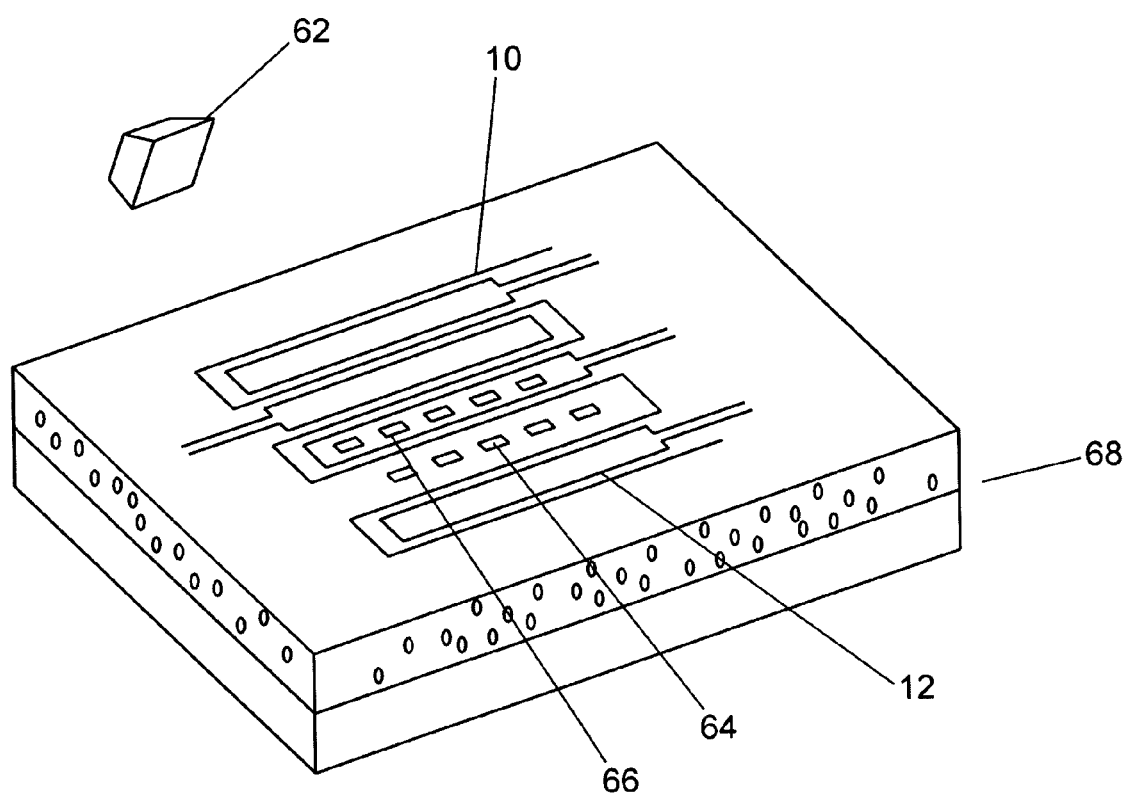
FIG. 11 shows an illustration of a hybrid sensor design along with a composite material having an embedded material.

In a similar fashion these quasistatic sensing methods can also be applied to thermal variants and hybrid configurations as described in U.S. patent application Ser. No. 11/036,780. As an example, consider FIG. 11, where current through a drive winding 10 can be used to create a magnetic field for sensing with inductive elements and also heating of the test material 68. Typically, the heating effect is accomplished with a lower excitation frequency than the signal used to measure the inductive properties of the test material. The heating of the drive winding could be through resistive losses in the winding itself or through the induced eddy currents in the test material. In addition, one or more thermal sense elements 64 can be placed in the vicinity of the drive winding to sense the temperature of the test material. These thermal sense elements can be thermistors, thermocouples, or other temperature sensitive devices. For example, pyroelectric sensing elements, described for example in U.S. Pat. Nos. 4,332,157, 4,453,405, and 4,551,425, and can be used in the thermal regime to provide a voltage in response to a temperature gradient. The sense elements 66 can also be intermingled with the inductive sense elements. Furthermore, the temperature of the test material can also be varied with alternative sources 62 such as heat lamps or lasers typical of other thermal nondestructive inspection methods. Thermoelectric sensors that combine thermal and electric field sensing modes are also possible. An example material is a glass fiber or ceramic matrix composite (CMC) where the constituent materials have a relatively low electrical conductivity so that magnetic field sensors are not sensitive to the material condition. These sensors can provide information about the properties of the embedded fibers, or even coatings on the fibers that may be added to enhance the observability of the bond integrity state with the matrix, the porosity, the presence of delamination, and the quality of the bond between the fibers and the host matrix for monitoring and control purposes.

These methods can also be extended to the methods of embedding state sensitive material layers as described in U.S. patent application Ser. No. 10/937,105, filed on Sep. 8, 2004, the entire teachings of which are incorporated herein by reference, for process control. This includes burying magnetic materials between layers and monitoring with either remote or embedded sensors. For example, the permeability of magnetic materials such as nickel and cobalt varies with stress, and nickel is used in fuel cells as an electrode material. However, the Curie point for nickel, above which it is nonmagnetic, is 358° C. Since SOFCs typically operate near 1000° C., the magnetic permeability of the nickel is not useful for monitoring the internal stresses or temperature. In contrast, cobalt has a Curie point of 1131° C., so that the magnetomechanical effect should persist at typical SOFC operating temperatures. This cobalt can be used as an electrode material itself or it can be deposited on another material near the electrode interfaces. The cobalt could even be deposited onto the nickel electrodes. Furthermore, the conductivity and permeability may also change with temperature, so that both the temperature and the stress can be measured over a wide range of temperatures.

Another aspect of this invention is directed toward the profiling and mapping of residual stress resulting from performing a process on a material. An example is shot peening, machining, grinding, or some other cold work process on a conducting and/or magnetically permeable material. These processes often result in a residual stress profile or distribution with depth away from the surface where the process was performed. Thus, even though the material may have initially been nominally homogeneous or uniform with depth, the process caused a change in a property distribution with depth.

Figure 12:
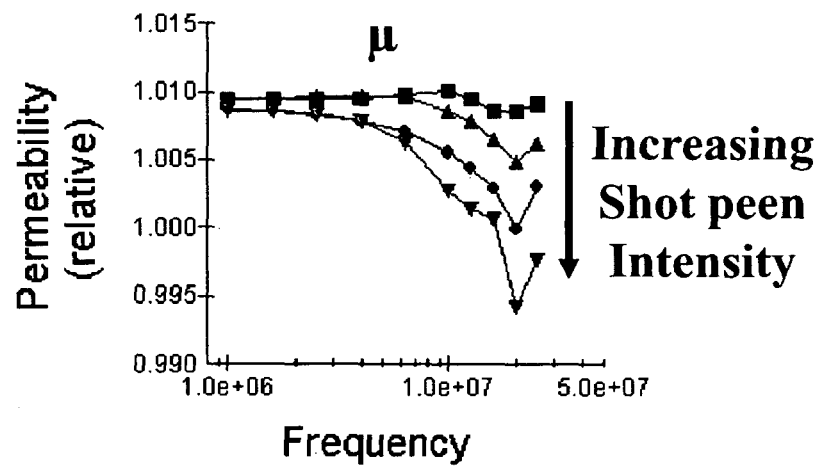
FIG. 12 shows an effective permeability plot as the frequency and shot peen intensity is varied assuming a constant conductivity.
Figure 13:
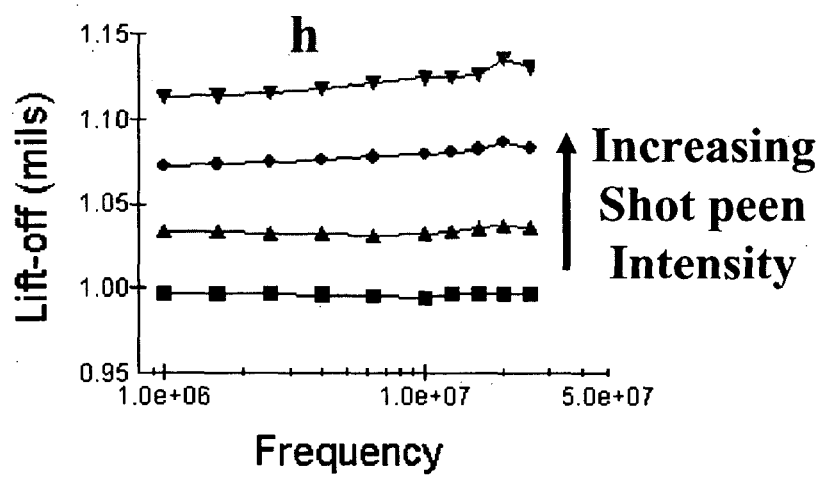
FIG. 13 shows an effective lift-off plot as the frequency and shot peen intensity is varied assuming a constant conductivity.

As an example, this stress profiling method can be used to qualify the shot peening process in relative low magnetic permeability materials. Many Nickel-based alloys and other materials begin with relatively low magnetic permeability before shot peening. For example, in IN718 or IN100 alloys the relative permeability is on the order of 1.01. At high frequency, for these alloys, shot peening decreases the permeability to ~1.00, as shown in FIG. 12. The effective lift-off, shown in FIG. 13, also varies with shot peening intensity. These effects can be used to qualify shot peen intensity. At sufficiently high frequencies, the magnetic field is confined near the surface of the MUT and reflects mainly the stress of the surface region. At lower frequencies, the magnetic field can penetrate through this region and the average or effective property (permeability or conductivity) approaches the bulk value. The response is measured as a function of frequency and used to estimate one or more properties of the material with a model that represents the stress variation in the MUT as a surface layer or a predetermined distribution of properties as a function of depth. Grid methods used to estimate the properties of the layer, lift-off and the substrate, or the parameters of the distribution.

For monitoring the stress distribution, the spatial property distribution as a function of depth can be split into several predetermined component layers. An example multiple layer distribution is shown in FIG. 2, where the outer layer may be relatively thin and can represent a machining affected zone. The middle and inner layers can reflect different portions of the deeper residual stress layer resulting from the cold work processing. Representative thicknesses of the machining affected zone are 0.0005 to 0.002 in. and for the residual stress layer are 0.001 to 0.005 in., but the thicknesses will depend upon the material type and the cold work (e.g., shot peening) intensity. The properties of the different layers can be determined independently, possibly with assumed thicknesses, so that the cold work process intensity itself is then correlated with the properties, such as the magnetic permeability or conductivity, of the residual stress layer. The properties can be determined using the grid methods and precomputed databases of responses. To help to isolate the properties of the residual stress layer, the properties of the test material can be monitored as the process is being performed, and the process conditions adjusted to ensure proper states are being achieved. Anisotropy in the properties can be measured with sensors having a directional bias, such as those having a linear, rectangular, or elliptical drive windings.

While the inventions have been particularly shown and described with reference to preferred embodiments thereof, it will be understood to those skilled in the art that various changes in form and details may be made therein without departing from the spirit and scope of the invention as defined by the appended claims.

What is claimed is:

1. A method of controlling a process of manufacturing a material, the method comprising:
   providing a sensor proximate to the material, the material having a plurality of components comprising a first component having a first material property measurable by the sensor and a second component having a, second material property measurable by the sensor;
   monitoring a response of the sensor during manufacturing of the material,
   using the sensor response and a precomputed database to estimate a value of the first material property for the first component;
   using the sensor response and the precomputed database to estimate a value of the second material property for the second component;
   estimating a value of a state of the material using at least one of the value of the first material property for the first component and the value of the second material property for the second component, and
   using the estimated value of the state of the material to support control decisions in the manufacturing process.

2. The method as claimed in claim 1 wherein the state is the temperature at the interface between the first component and second component.

3. The method as claimed in claim 1 wherein the state is a cure state.

4. The method as claimed in claim 1 wherein the sensor is a dielectric sensor.

5. The method as claimed in claim 1 wherein the sensor is a magnetic field sensor.

6. The method as claimed in claim 1 wherein the sensor is thermal.

7. The method as claimed in claim 1 wherein the first component is a plurality of fibers, the second component is a matrix, and the state is bond integrity between the plurality of fibers and the matrix.

8. The method as claimed in claim 7, wherein the plurality of fibers have a coating that enhances observability of a bond between the plurality of fibers and the matrix.

9. The method as claimed in claim 1 wherein the first component is embedded in a matrix of the second component.

10. The method of claim 1, wherein the precomputed database relates the sensor response to the first material property to estimate the value of the first material property of the first component and further relates the value of the first material property to the state of the material to estimate the value of the state of the material.

11. The method as claimed in claim 1 wherein the first component is a first layer of the material immediately proximate to the sensor and the second component is an additional layer of the material farther from the sensor.

12. The method as claimed in claim 11 wherein the first and additional layers are representations of process affected layers.

13. The method as claimed in claim 12 wherein the process affected layers result from a residual stress distribution.

14. The method as claimed in claim 11 wherein the sensor is permanently mounted.

15. The method as claimed in claim 14 wherein the sensor is embedded between material layers.

16. The method as claimed in claim 11 wherein at least one layer is an interface layer.

17. The method as claimed in claim 16 wherein the state is the integrity of the interface layer bond.

18. The method as claimed in claim 11 wherein the control decision requires an action to move the value of the state towards a goal value.

19. The method as claimed in claim 18 wherein the goal value is a time varying goal.

20. The method as claimed in claim 18 wherein the goal value is a spatially varying goal value.

21. The method as claimed in claim 18 wherein the goal value is a temperature value 22. A method of controlling a manufacturing process, the method comprising:
   providing a sensor proximate to a composite material, the composite material comprising fibers embedded in a matrix, the fibers having a first material property measurable by the sensor and the matrix having a second material property that is measurable by the sensor;
measuring a response of the sensor during the manufacturing process;
estimating a first value of the first material property for the fibers and not the matrix using the sensor response and a precomputed database;
estimating a second value of the second material property for the matrix and not the fibers using the sensor response and the precomputed database;
estimating a value of a state of the composite material from at least one of the first value and the second value; and
using the estimated value of the state of the composite material to support a control decision during the manufacturing process.

* * * * *